US00PP20322P2

(12) United States Plant Patent
Bloom

(10) Patent No.: US PP20,322 P2
(45) Date of Patent: Sep. 15, 2009

(54) ***DICENTRA* PLANT NAMED 'SPRING MAGIC'**

(50) Latin Name: *Dicentra formosa*
Varietal Denomination: Spring Magic

(76) Inventor: Adrian Bloom, 1Foggy Bottom, Bressingham, Diss, Norfolk IP22 2AB (GB)

( * ) Notice: Subject to any disclaimer, the term of this patent is extended or adjusted under 35 U.S.C. 154(b) by 0 days.

(21) Appl. No.: 12/218,285

(22) Filed: Jul. 14, 2008

(51) Int. Cl.
*A01H 5/00* (2006.01)

(52) U.S. Cl. ..... Plt./426

(58) Field of Classification Search ..... Plt./426
See application file for complete search history.

*Primary Examiner*—Kent L Bell
(74) *Attorney, Agent, or Firm*—C. A. Whealy

(57) ABSTRACT

A new and distinct cultivar of *Dicentra* plant named 'Spring Magic', characterized by its upright and rounded plant habit; freely flowering habit; light pink-colored flowers; and good garden performance.

1 Drawing Sheet

Botanical designation: *Dicentra formosa.*
Cutlivar denomination: 'SPRING MAGIC'.

BACKGROUND OF THE INVENTION

The present invention relates to a new and distinct cultivar of *Dicentra,* botanically known as *Dicentra formosa* and hereinafter referred to by the name 'Spring Magic'.

The new *Dicentra* originated from an open-pollination in Bressingham, Diss, Norfolk, United Kingdom, of an unnamed selection of *Dicentra formosa,* not patented, as the female, or seed, parent with an unknown selection of *Dicentra formosa* as the male, or pollen, parent. The new *Dicentra* was discovered and selected by the Inventor as a single flowering plant within the progeny of the stated open-pollination in a controlled outdoor nursery environment in Bressingham, Diss, Norfolk, United Kingdom in April/May, 1998.

Asexual reproduction of the new *Dicentra* by cuttings in a controlled greenhouse environment in Bressingham, Diss, Norfolk, United Kingdom since June, 1998, has shown that the unique features of this new *Dicentra* are stable and reproduced true to type in successive generations.

SUMMARY OF THE INVENTION

Plants of the new *Dicentra* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Spring Magic'. These characteristics in combination distinguish 'Spring Magic' as a new and distinct cultivar of *Dicentra:*

1. Upright and rounded plant habit.
2. Freely flowering habit.
3. Light pink-colored flowers.
4. Good garden performance.

Plants of the new *Dicentra* differ from plants of the female parent selection in the following characteristics:

1. Plants of the new *Dicentra* have darker-colored leaves than plants of the female parent selection.
2. Plants of the new *Dicentra* and the female parent selection differ in flower color as plants of the female parent selection have darker pink-colored flowers.

Plants of the new *Dicentra* can also be compared to plants of *Dicentra formosa* 'Bacchanal', not patented. Plants of the new *Dicentra* and 'Bacchanal' differ in the following characteristics:

1. Plants of the new *Dicentra* have darker-colored leaves than plants of 'Bacchanal'.
2. Plants of the new *Dicentra* and 'Bacchanal' differ in flower color as plants of 'Bacchanal' have darker pink-colored flowers.

BRIEF DESCRIPTION OF THE PHOTOGRAPHS

The accompanying colored photographs illustrate the overall appearance of the new Dicentra, showing the colors as true as it is reasonably possible to obtain in colored reproductions of this type. Colors in the photographs may differ slightly from the color values cited in the detailed botanical description which accurately describe the colors of the new *Dicentra.*

The photograph at the bottom of the sheet comprises a side perspective view of a typical flowering plant of 'Spring Magic' grown in a container.

The photograph at the top of the sheet is a close-up view of typical inflorescences of 'Spring Magic'.

DETAILED BOTANICAL DESCRIPTION

The aforementioned photographs and following observations, measurements and values describe plants grown in Lancaster, Pa. under commercial practice during the winter and early spring in a polyethylene-covered greenhouse with day temperatures ranging from 2° C. to 10° C. and night temperatures ranging from 2° C. to 7° C. Plants were two months from planting when the photographs and description were taken. In the following description, color references are made to The Royal Horticultural Society Colour Chart, 2001 Edition, except where general terms of ordinary dictionary significance are used.

Botanical classification: *Dicentra formosa* 'Spring Magic'.

Parentage:

*Female, or seed, parent.*—Unnamed selection of *Dicentra formosa,* not patented.

*Male, or pollen, parent.*—Unknown selection of *Dicentra formosa,* not patented.

Propagation:

*Type.*—By cuttings.

*Time to initiate roots plant, summer.*—About 10 days at 21° C. to 25° C.

*Time to produce a rooted plant, summer.*—About two months at 21° C. to 25° C.

*Root description.*—Fleshy; white, close to 158B, in color.

*Rooting habit.*—Freely branching; dense.

Plant description:

*Plant form/habit.*—Perennial container or garden plant. Upright and rounded plant habit; leaves and flowering shoots developing from a basal rosette; moderately vigorous growth habit.

*Plant height.*—About 18 cm.

*Plant width* (*spread*).—About 16 cm.

*Leaf description.*—Arrangement: Developing from a basal rosette; alternate, simple. Length: About 5.4 cm. Width: About 7.2 cm. Shape: Roughly deltoid; deeply incised. Apex: Acute to emarginate. Base: Cuneate. Margin: Deeply incised. Texture, upper and lower surfaces: Smooth, glabrous. Venation pattern: Pinnate. Color: Developing leaves, upper surface: Close to 144A. Developing leaves, lower surface: Close to 146B. Fully expanded leaves, upper and lower surfaces: Close to N138B; venation, close to N138B. Petiole: Length: About 10.3 cm. Diameter: About 1.5 mm. Texture, upper and lower surfaces: Smooth, glabrous. Color, upper surface: Close to 197A. Color, lower surface: Close to 177B.

Flower description:

*Flower type/habit.*—Single flattened cordate/saccate-shaped flowers arranged in loose racemes arising from the central crown and holding the flowers above the foliage on strong peduncles; flowers nodding. Freely flowering habit with about six to ten open flowers per inflorescence.

*Fragrance.*—None detected.

*Natural flowering season.*—Continuously flowering during June.

*Postproduction longevity.*—Flowers maintain good substance and color for about five days on the plant; flowers not persistent.

*Flower buds.*—Height: About 8 mm. Diameter: About 3 mm. Shape: Lanceolate. Color: Towards the apex, close to 195B; mid-section, close to 36D; towards the base, close to 36A.

*Inflorescence height.*—About 6 cm.

*Inflorescence diameter: About* 3.7 cm.

*Flower length.*—About 1.7 cm.

*Flower diameter.*—About 9 mm.

*Flower depth.*—About 5 mm.

*Petals.*—Quantity per flower: Typically four; two outer saccate petals fused in to a cordate structure and two inner petals fused at the apices. Length, outer petals: About 1.7 cm. Length, inner petals: About 8 mm. Width, outer petals: About 6 mm. Width, inner petals: About 2 mm. Shape, outer petals: Roughly elliptical. Shape, inner petals: Roughly lanceolate. Apex: Acute. Margin: Entire. Texture, upper and lower surfaces: Smooth, glabrous. Color: Developing and fully expanded petals, outer surface: Close to 65B; towards the apex, close to 65C to 65D; color becoming closer to 56D with development. Developing and fully expanded petals, inner surface: Close to 65D; color becoming closer to 56D with development.

*Sepals.*—Quantity per flower: Typically two; opposite, closely appressed to base of corolla. Length: About 2 mm. Width: About 2 mm. Shape: Elliptical. Apex: Acute. Base: Truncate. Margin: Entire. Texture, upper and lower surfaces: Smooth, glabrous. Color, upper surface: Close to 63D. Color, lower surface: Close to 182D.

*Peduncles.*—Length: About 16 cm. Diameter: About 1 mm. Angle: Mostly erect. Strength: Strong. Texture: Smooth, glabrous. Color: Close to 146B.

*Pedicels.*—Length: About 1.5 cm. Diameter: Less than 1 mm. Angle: About 30° to 45° from vertical; pedicels eventually drooping with weight of fully developed flowers. Strength: Strong. Texture: Smooth, glabrous. Color: Close to 182B.

*Reproductive organs.*—Stamens: Quantity per flower: Typically four. Filament length: About 1.8 cm. Filament color: Close to 49D. Anther shape: Rounded. Anther length: Less than 1 mm. Anther color: Close to 160A. Pollen amount: Scarce. Pollen color: Close to 160A. Pistils: Quantity per flower: One. Pistil length: About 1.4 cm. Stigma shape: Fan-shaped, flattened. Stigma color: Close to 155D. Style length: About 5 mm. Style color: Close to 145A. Ovary color: Close to 138A.

*Seed/fruit.*—Seed and fruit development have not been observed.

Disease/pest resistance: Plants of the new *Dicentra* have been not been observed to be resistant to pathogens and pests common to *Dicentra.*

Garden performance: Plants of the new *Dicentra* have been observed to have good garden performance and tolerate rain, wind and temperatures ranging from about −10° C. to about 35° C.

It is claimed:

1. A new and distinct *Dicentra* plant named 'Spring Magic' as illustrated and described.

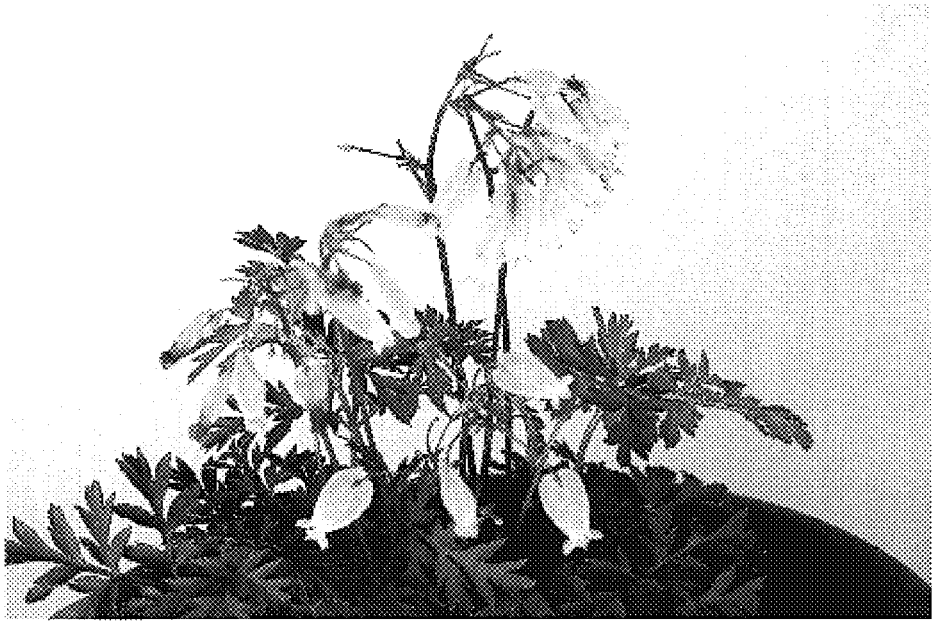
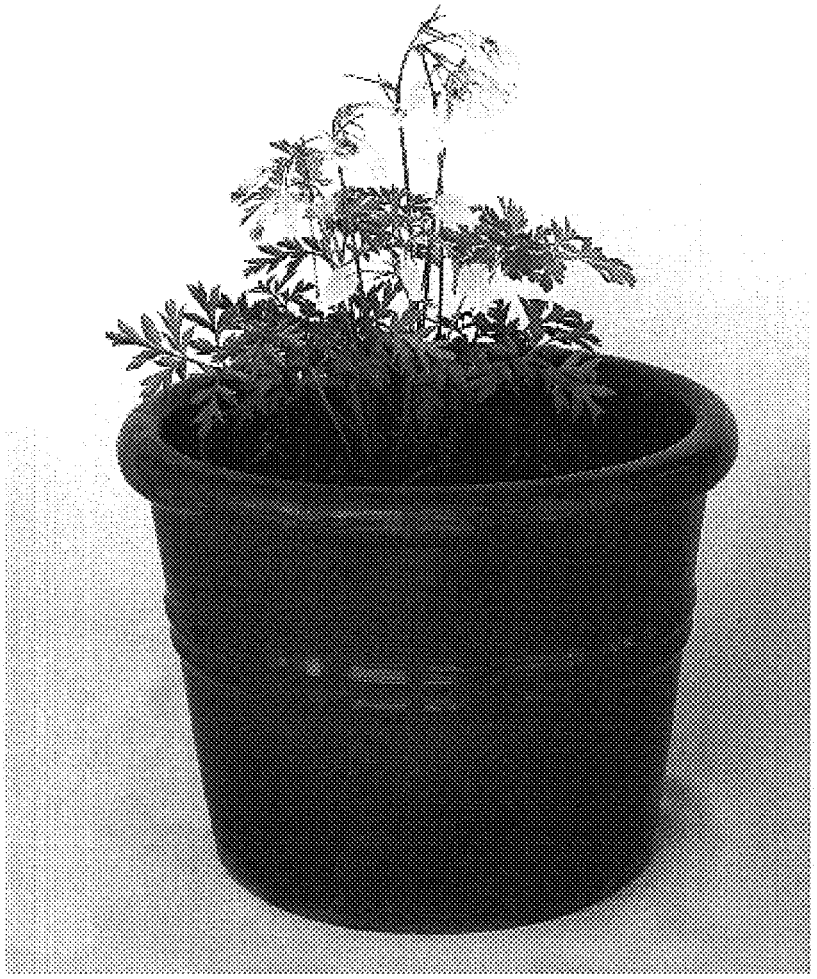

* * * * *